United States Patent [19]

Wetzel et al.

[11] 4,289,775
[45] Sep. 15, 1981

[54] PENICILLINS

[75] Inventors: Bernd Wetzel; Eberhard Woitun, both of Biberach an der Riss; Wolfgang Reuter, Laupertshausen; Roland Maier, Biberach an der Riss; Uwe Lechner, Ummendorf; Hanns Goeth, Biberach an der Riss, all of Fed. Rep. of Germany

[73] Assignee: Karl Thomae GmbH, Biberach an der Riss, Fed. Rep. of Germany

[21] Appl. No.: 149,839

[22] Filed: May 14, 1980

Related U.S. Application Data

[63] Continuation of Ser. No. 117,103, Jan. 31, 1980, abandoned.

Foreign Application Priority Data

[30] Mar. 15, 1979 [DE] Fed. Rep. of Germany ....... 2910190

[51] Int. Cl.³ ....... A61R 31/505; C07D 499/68; C07D 499/70
[52] U.S. Cl. .................................. 424/251; 260/239.1
[58] Field of Search ....................... 260/239.1; 424/251

[56] References Cited

U.S. PATENT DOCUMENTS

| | | | | |
|---|---|---|---|---|
| 3,308,023 | 3/1967 | Russell | | 260/239.1 |
| 3,352,851 | 11/1967 | Fosker | | 260/239.1 |
| 4,031,230 | 6/1977 | Gottschlich et al. | | 260/239.1 |
| 4,038,271 | 7/1977 | Breur et al. | | 260/239.1 |

*Primary Examiner*—Natalie Trousof
*Assistant Examiner*—Vera C. Clarke
*Attorney, Agent, or Firm*—Hammond & Littell, Weissenberger & Muserlian

[57] ABSTRACT

Compounds of the formula

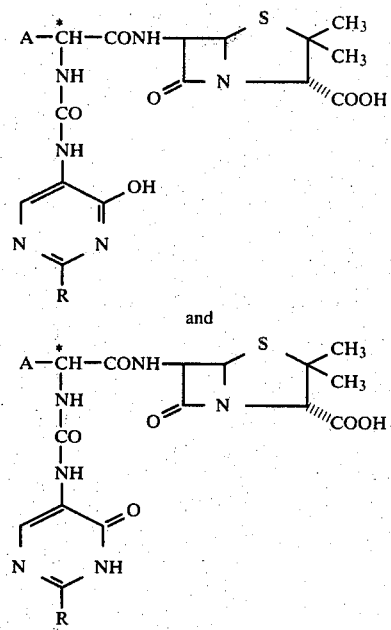

wherein

A is phenyl, p-hydroxy-phenyl, 2-thienyl, 3-thienyl or 3,4-disubstituted phenyl, where the substituents, which may be identical to or different from each other, are each chlorine, hydroxyl or methoxy;

R is —NH—Z—X;

Z is straight or branched alkylene of 1 to 6 carbon atoms or cycloalkylene of 3 to 6 carbon atoms;

X is cyano, hydroxyl, mercapto, aminocarbonyl, aminosulfonyl,

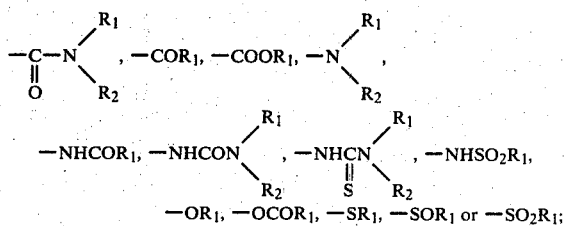

$R_1$ is straight or branched alkyl of 1 to 4 carbon atoms or phenyl;

$R_2$ is hydrogen or alkyl of 1 to 4 carbon atoms; and $R_1$ and $R_2$, together with an adjacent nitrogen atom to which they are attached, form a 3- to 6-membered heterocyclic ring;

and non-toxic, pharmacologically acceptable salts thereof formed with inorganic or organic bases.

6 Claims, No Drawings

PENICILLINS

This is a continuation of copending application Ser. No. 117,103, filed Jan. 31, 1980, now abandoned.

This invention relates to novel penicillins and salts thereof, to methods of preparing these compounds, to pharmaceutical compositions containing the compounds as active ingredients, and to methods of using them as antibiotics.

More particularly, the present invention relates to compounds of the tautomeric formulas

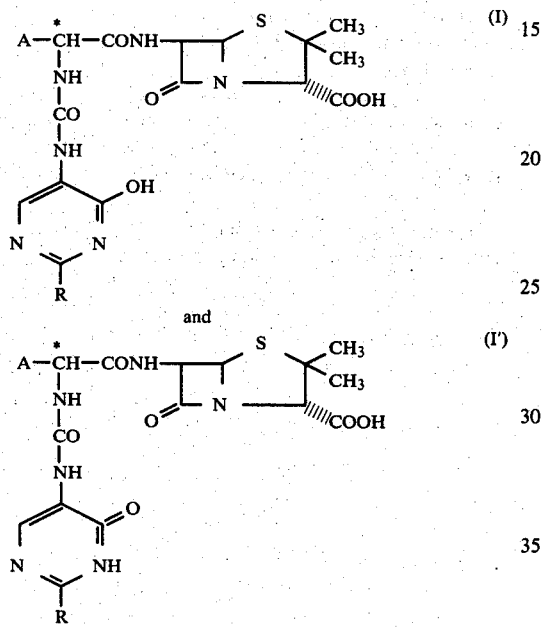

wherein
A is phenyl, p-hydroxy-phenyl, 2-thienyl, 3-thienyl or 3,4-disubstituted phenyl, where the substituents, which may be identical to or different from each other, are each chlorine, hydroxyl or methoxy;
R is —NH—Z—X;
Z is straight or branched alkylene of 1 to 6 carbon atoms or cycloalkylene of 3 to 6 carbon atoms;
X is cyano, hydroxyl, mercapto, aminocarbonyl, aminosulfonyl,

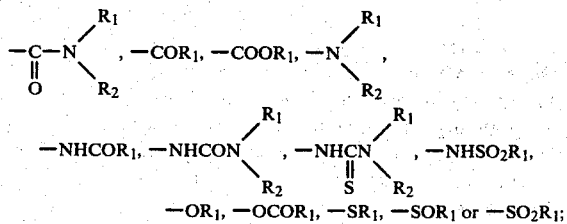

$R_1$ is straight or branched alkyl of 1 to 4 carbon atoms or phenyl;
$R_2$ is hydrogen or alkyl of 1 to 4 carbon atoms; and $R_1$ and $R_2$, together with an adjacent nitrogen atoms to which they are attached, form a 3- to 6- membered heterocyclic ring;
and non-toxic, pharmacologically acceptable salts thereof formed with inorganic or organic bases.

A preferred sub-genus thereunder is constituted by compounds of the formula I or I'
wherein
A is phenyl or p-hydroxy-phenyl;
R is 4'-hydroxy-cyclohexylamino,

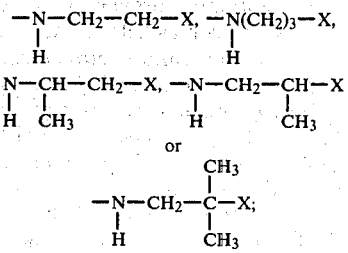

X is hydroxyl, methoxy, ethoxy, methoxycarbonyl, ethoxycarbonyl, methylcarbonyl, ethylcarbonyl, methylmercapto, ethylmercapto, aminocarbonyl, aminosulfonyl, acetylamino, methylsulfinyl or ethylsulfinyl;
and non-toxic, pharmacologically acceptable salts thereof formed with inorganic or organic bases.

With respect to the chiral center C*, the compounds of the formula I or I' may occur in the two possible R- and S-configurations, but also as a mixture of these two configurations. Especially preferred are those compounds of the formula I or I' which have the D=R-configuration.

The compounds of the present invention may be prepared by the following methods:

Method A

By reacting a compound of the formula

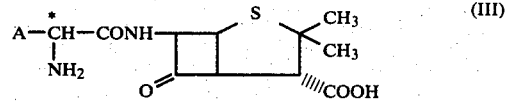

wherein A has the same meanings as in formula I or I', with a pyrimidine derivative of the formula

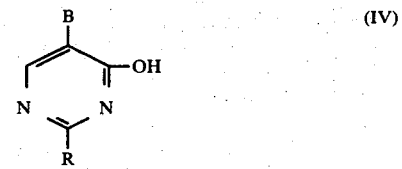

wherein
R has the same meanings as in formula I or I',
B is —NCO or a reactive derivative of —NHCOOH, such as —NHCOCl, —NHCOBr or

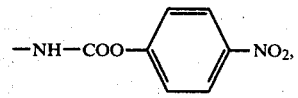

where —NHCOCl is particularly preferred. Also mixtures of two or more pyrimidine derivatives of the formula IV may be used, where B in one of the mixture components has one of the above-defined meanings, such as —NCO and B in the other component or components has another of the abovedefined meanings, such as NHCOCl.

The starting compounds of the formula III may be used in the form of their inorganic or organic salts, for instance, as the triethylammonium salt or the sodium salt. The reaction may be carried out in any desired mixture of water and those organic solvents which are miscible with water, such as ketones, for example acetone; cyclic ethers, for example tetrahydrofuran or dioxane; nitriles, for example acetonitrile, formamides, for example dimethylformamide or dimethylsulfoxide; or alcohols, for example isopropanol; or in hexametapol. The pH of the reaction mixture is preferably kept, by addition of a base or by use of a buffer solution, in a range of from 2.0 to 9.0, preferably between a range of from 6.5 to 8.0. It is also possible to carry out the reaction in anhydrous organic solvents, for instance, halogenated hydrocarbons such as chloroform or methylene chloride, by addition of bases, preferably triethylamine, diethylamine or N-ethylpiperidine.

The reaction may also be carried out in a mixture of water and a water-immiscible solvent, for example an ether, such as diethylether; halogenated hydrocarbons, such as chloroform or methylene chloride; carbon disulfide; ketones, such as isobutylmethylketone; esters, such as ethyl acetate; or aromatic solvents, such as benzene. Such reactions are preferably carried out while vigorously stirring and preferably, by addition of a base or by use of a buffer solution, at a pH of from 2.0 to 9.0, preferably from 6.5 to 8.0. The reaction can also be carried out in water in the presence of either an organic or inorganic base or of a buffer agent.

If a silyl derivative of the compound of the formula III, for example the mono- or di-trimethylsilyl derivative, is used as the starting material for the process according to the invention, and is reacted with a compound of the formula IV, the reaction is preferably effected in the presence of an anhydrous solvent free of hydroxyl groups, for example in a halogenated hydrocarbon, such as methylene chloride or chloroform, benzene, tetrahydrofuran, acetone or dimethylformamide, etc. The addition of a base is not necessary, but can be of advantage in certain cases, to improve the yield and the purity of the products. Suitable bases include, for example tertiary aliphatic and aromatic amines such as pyridine or triethylamine, or sterically hindered, difficultly acylatable secondary amines, such as dicyclohexylamine, Other examples of esters of the compound of the formula IV which may be used are those well known in the field of semi-synthetic penicillins. Such esters include, for example, the trityl ester, the p-nitrobenzyl ester and the phenacyl ester. Subsequent to the reaction these ester derivatives may, where necessary, be converted into the desired penicillin by methods well known in the art. The amount of base preferably used in the above reactions is generally dictated by the desirability of maintaining a particular pH. Where pH measurement and adjustment is not carried out or is not possible or appropriate due to lack of sufficient water in the solvent, then, when a compound of the formula II is used, preferably from 1.0 to 2.0 mol equivalents of base are employed. When a silyl derivative of the compound of the formula II is used, up to one mol equivalent of base is employed.

In general, such bases may be any of those which are commonly used in organic chemistry as organic or inorganic bases, such as alkali metal hydroxides, alkaline earth hydroxides, alkaline earth metal oxides, alkali metal and alkaline earth metal carbonates and bicarbonates, ammonia, primary, secondary and tertiary aliphatic and aromatic amines, as well as heterocyclic bases. Such bases include, for example, sodium, potassium or calcium hydroxide, calcium oxide, sodium or potassium carbonate, sodium or potassium bicarbonate, ethylamine, methylethylamine, triethylamine, hydroxyethylamine, aniline, pyridine and piperidine. When using silylated starting materials, however, the above-mentioned restrictions concerning the kind of base used should be noted.

As a buffer solution, any of the conventional buffer mixtures can be used, such as phosphate buffer, citrate buffer and tris-(hydroxymethyl)-aminomethane buffer.

The reaction temperature can be varied over a wide range. In general, it is preferred to work at $-20°$ to $+50°$ C., preferably at $0°$ to $+20°$ C.

The reaction partners of the formulas II and III can be reacted with each other in equimolar amounts. However, in certain cases it may be of advantage to use one of the reactants in excess in order to facilitate the purification of the end product or to increase the yield.

Method B

By reacting of a ureido-carboxylic acid of the formula

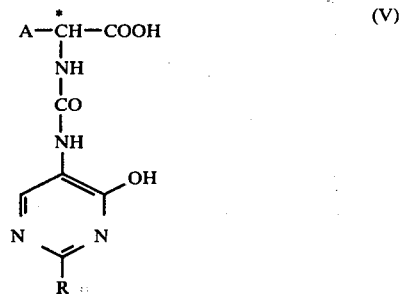

(V)

wherein A and R have the meanings previously defined, or a salt or reactive derivative thereof, with the 6-aminopenicillanic acid of the formula

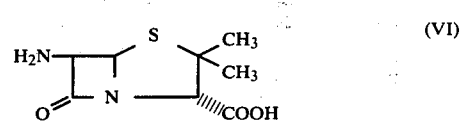

(VI)

an inorganic or organic salt thereof, or a derivative thereof which is easily transformable into the 6-aminopenicillanic acid. The reaction product obtained is optionally subsequently hydrolyzed into a penicillin of the formula I or I' or catalytically hydrogenated.

Examples of suitable reactive derivatives of the ureido-carboxylic acids of the formula V are acid anhydrides, such as those derived from chloroformates, for instance ethyl chloroformate, isobutyl chloroformate, reactive esters such as the p-nitrophenyl ester or the N-hydroxysuccinimide ester, or the reactive amides thereof such as the N-carbonylimidazole, but also the acid halides thereof such as the corresponding acid chloride or the acid azides thereof. In principle, however, all methods can be used which are known in β-lactam chemistry.

The 6-amino-penicillanic acid is advantageously used in the form of its derivatives, for example the trimethylsilyl ester, trityl ester, p-nitrobenzyl ester, phenacyl ester or the O,N-bis-trimethylsilyl derivative. These derivatives are reacted preferably in the presence of an aprotic solvent, such as methylene chloride or tetrahydrofuran. The 6-amino-penicillanic acid can also be reacted in the form of its salts, for example the triethylammonium salt. In such cases the reaction is preferably carried out in the presence of methylene chloride, an aprotic solvent, an aqueous medium or an aqueous-organic solvent, such as tetrahydrofuran-water mixtures.

The ureido-carboxylic acid, its salt or its reactive derivative is reacted with the 6-amino-penicillanic acid or its derivative in a solvent at temperatures between $-40°$ C. and $+40°$ C., optionally in the presence of a base. If, for example, an anhydride of the ureido-carboxylic acid, such as the anhydride with ethyl chloroformate, is reacted with a derivative of the 6-amino-penicillanic acid, the reaction is carried out while cooling, for example at $-10°$ to $+10°$ C., in the presence of a tertiary amine such as triethylamine or N,N-dimethylaniline, and in a solvent such as acetone, tetrahydrofuran, dimethylformamide, chloroform, dichloromethane, hexametapol or a mixture of these solvents.

If an N-hydroxysuccinimide ester of the ureidocarboxylic acid is reacted with the 6-amino-penicillanic acid, the reaction is preferably carried out at 0° to 20° C. in the presence of a base, such as triethylamine, and in a solvent such as dimethylformamide, dichloromethane, dioxane or a mixture of such solvents.

The reaction of a ureido-carboxylic acid of the formula IV or a salt thereof with the 6-amino-penicillanic acid or a salt thereof is advantageously carried out in the presence of a condensation agent, for example in the presence of N,N'-dicyclohexylcarbodiimide.

If a derivative of the 6-amino-penicillanic acid is used, for example one of the above-mentioned esters, a product is obtained which may, depending on the reaction conditions employed, still contain the ester function. Such a reaction product may, however, be easily converted into the penicillin of the formula I.

If, for example, the carboxyl group of the 6-aminopenicillanic acid is present in the form of its silyl ester, this group may also be present in the product of the formula I obtained after the reaction, but may subsequently be removed by hydrolysis to form the compound of the formula I or I'. In other cases, for example if a p-nitrobenzyl ester is present, this p-nitrobenzyl ester group may be split off by hydrogenation to give the pencillin of the formula I or I'.

Further processing of the reaction mixture obtained in either method may be carried out according to methods well known in connection with β-lactam antibiotics, such as isolation and purification of the end products, liberation of the free acids from their salts, and the conversion of the acids into salts by means of inorganic or organic bases. Thus, for example, potassium or sodium salts are preferably formed by precipitation from an alcohol-ethereal solution of the free acid by addition of potassium or sodium 2-ethylhexanoate.

The starting compounds of the formula III are known from the literature; see, for example, E. H. Flynn, Cephalosporins and Penicillins, Academic Press, New York and London (1972).

The starting compounds of the formula IV may be obtained, for example, by reacting a corresponding 5-amino-pyrimidine of the formula

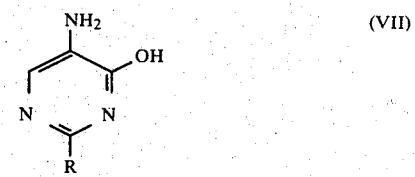

wherein R has the meaning previously defined, with phosgene. This reaction is preferably carried out in a solvent containing no hydroxyl groups, such as tetrahydrofuran, methylene chloride, chloroform, dimethoxyethane or hexametapol, at temperatures between $-40°$ and $+60°$ C., preferably between $-10°$ and $+20°$ C. It is, in general, advisable to bind the resultant hydrogen chloride by addition of equimolar amounts of an inert organic base, such as triethylamine or pyridine. Pyridine in excess may also serve as the solvent medium. If the amino-pyrimidines of the formula VII are difficultly soluble in one of the above-mentioned solvents, the phosgenation can also be carried out in heterogeneous phase. Furthermore, the amino-pyrimidines of the formula VII can, by treatment with a silylating agent such as hexamethyldisilazane, trimethylchlorsilane/triethylamine or trimethylsilyl-diethylamine, be converted into the single or multiple silylated aminopyrimidine, depending upon the number of exchangeable hydrogen atoms present in the molecule, which is easily soluble in the above-mentioned solvents. The thus obtained aminopyrimidine may then be reacted with phosgene to give the corresponding compound of the formula IV. Depending on the kind of solvent, temperature and amount and kind of base used, either mainly the corresponding isocyanate or carbamic acid halide or a mixture of these is obtained. Depending on the reaction conditions, the compound of the formula IV can in part by present as an isocyanate isomer, that is, a tetrahydrooxazolopyrimidine of the formula IVa.

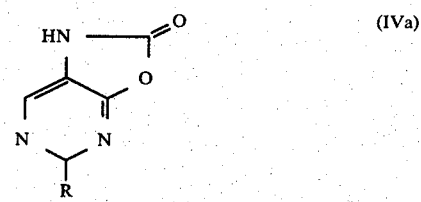

The starting compounds of the formula IV or mixtures thereof obtained by phosgenation as described above are in general readily soluble in the above-mentioned solvents, and after removal of excess phosgene they can be directly reacted without further purification with the corresponding penicillin derivative of the formula III.

The 5-amino-4-hydroxy-2-substituted pyrimidines of the formula VII can be prepared, for example, by reacting of 2-methylmercapto-4-hydroxy-5-nitro-pyrimidine of the formula VIII [see Vorbrüggen and Strehlke, Chem.Ber. 106, p. 3039 (1973)] with a substituted alkylamine of the formula IX, wherein X and Z have the meanings previously defined, and subsequent reduction of the nitro group of the obtained compound of the formula X by known methods, according to the following reaction sequence:

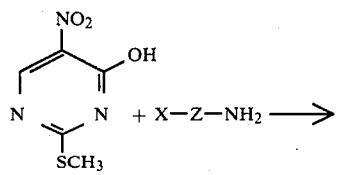

(VIII)       (IX)

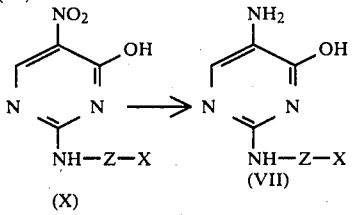

(X)    (VII)

To characterize the starting materials, the following are some representative examples of the formula VII which may be used:

5-Amino-4-hydroxy-2-(2'-hydroxyethylamino)-pyrimidine;
5-Amino-4-hydroxy-2-(3'-hydroxypropylamino)-pyrimidine;
5-Amino-4-hydroxy-2-(2'-hydroxypropylamino)-pyrimidine;
5-Amino-4-hydroxy-2-(2'-hydroxy-2'-methylpropylamino)-pyrimidine;
5-Amino-4-hydroxy-2-(2'-methoxyethylamino)-pyrimidine;
5-Amino-4-hydroxy-2-(2'-ethoxyethylamino)-pyrimidine;
5-Amino-4-hydroxy-2-(3'-methoxypropylamino)-pyrimidine;
5-Amino-4-hydroxy-2-(ethoxycarbonylmethylamino)-pyrimidine;
5-Amino-4-hydroxy-(2'-ethoxycarbonylethylamino)-pyrimidine;
5-Amino-4-hydroxy-(2'-ethylmercapto-ethylamino)-pyrimidine;
5-Amino-4-hydroxy-(2'-methylmercapto-ethylamino)-pyrimidine;
5-Amino-4-hydroxy-(2'-cyano-propylamino)-pyrimidine;
5-Amino-4-hydroxy-(4'-hydroxy-cyclohexylamino)-pyrimidine;
5-Amino-4-hydroxy-(2'-methylcarbonyl-ethylamino)-pyrimidine;
5-Amino-4-hydroxy-(3'-aminocarbonyl-propylamino)-pyrimidine;
5-Amino-4-hydroxy-(3'-aminosulfonyl-propylamino)-pyrimidine;
5-Amino-4-hydroxy-(2'-acetylamino-ethylamino)-pyrimidine;
5-Amino-4-hydroxy-(3'-methylsulfinyl-propylamino)-pyrimidine.

The ureido-carboxylic acids of the formula V may be obtained by reacting a pyrimidine derivative of the formula IV with a glycine derivative of the formula

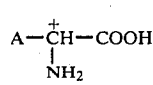

(XI)

wherein A has the meanings previously defined. The reaction is effected at temperatures between −20° C. and 40° C., preferably between 0° and +20° C., in a solvent. Examples of suitable solvents are mixtures of water and organic water-miscible solvents, such as acetone, tetrahydrofuran, dioxane, acetonitrile, dimethylformamide, ethanol or dimethylsulfoxide. Optionally the use of a halogen halide binding agent is necessary; such agents may include, for example, trialkylamines such as triethylamine, or inorganic bases such as dilute sodium hydroxide.

The following examples illustrate the present invention and will enable others skilled in the art to understand it more completely. It should be understood, however, that the invention is not limited solely to the particular examples given below.

"Ampicillin" is α-aminobenzylpenicillin, and "amoxycillin" is α-amino-p-hydroxy-benzylpenicillin with the D=R configuration in the side chain.

I. PREPARATION OF STARTING COMPOUNDS

EXAMPLE A

5-Amino-4-hydroxy-2-(2'-methoxyethylamino)-pyrimidine (a) 5.03 gm (0.025 mol) of 2-ethylmercapto-4-hydroxy-5-nitro-pyrimidine in 100 ml of ethanol were refluxed with 3.76 gm (0.05 mol) of 2-methoxyethylamine for 16 hours. After cooling, the precipitated product was suction-filtered off, washed with a little ethanol and dried. Then, the substance was stirred with water and acidified with 2 N hydrochloric acid. After suction-filtering, the reaction product was washed with water and dried.

Yield: 3.9 gm (73% of theory) M.p.: 222° C.
Analysis: Calc.: C-39.25%; H-4.71%; N-26.16%; Found: C-38.76%, H-4.91%; N-26.10%.

(b) 3.9 gm of the thus obtained nitro compound in 200 ml of ethanol were hydrogenated with 3.9 gm of Raney nickel for 2 hours at 50° C. After distilling off the ethanol, the remaining oily product was quickly filtered over a short silicagel column (eluant: methylene chloride/methanol, 3:1). The obtained product (2.1 gm=63%) liquefied in the air to form a greasy substance.

Analysis: Calc.: C-45.64%; H-6.57%; N-30.42%; Found: C-44.97%; H-6.88%; N-29.11%.

IR spectrum: 3260, 3050 (broad), 2960, 2930, 2880, 1670, 1610, 1580, 1110 cm$^{-1}$;

NMR spectrum (DMSO+CD$_3$OD) signals at ppm: 3.3 (s,3H), 3.5 (m,4H), 7.05 (s,1H).

Analogously, the following aminopyrimidines of the formula VII were synthesized:

| R | Yield | Analysis | | |
|---|---|---|---|---|
| —NH(CH$_2$)$_2$OC$_2$H$_5$ | 47% calc.: | C-48.47%; | H-7.12%; | N-28.27% |
| | found: | C-47-91%; | H-7.24%; | N-27.95% |
| —NH(CH$_2$)$_2$OC$_3$H$_7$ | 51% calc.: | C-50.93%; | H-7.60%; | N-26.40% |
| | found: | C-51.01%; | H-8.27%; | N-25.95% |

-continued

| R | Yield | Analysis | | |
|---|---|---|---|---|
| —NH(CH₂)₂OC₄H₉ | 41% | calc.: C-53.07%; | H-8.02%; | N-24.76% |
| | | found: C-52.81%; | H-8.17%; | N-24.01% |
| —NH(CH₂)₃OCH₃ | 38% | calc.: C-48.47%; | H-7.12%; | N-28.27% |
| | | found: C-48.07%; | H-6.99%; | N-27.75% |
| —NH(CH₂)₃OC₂H₅ | 52% | calc.: C-50.93%; | H-7.60%; | N-26.46% |
| | | found: C-50.42%; | H-7.87%; | N-26.12% |
| —NH(CH₂)₃OC₃H₇ | 50% | calc.: C-53.07%; | H-8.02%; | N-24.76% |
| | | found: C-53.01%; | H-8.12%; | N-24.04% |
| —NH(CH₂)₂OC₆H₅ | 28% | calc.: C-58.52%; | H-5.73%; | N-22.75% |
| | | found: C-58.43%; | H-5.87%; | N-22.50% |
| —NH(CH₂)₂OH | 40% | calc.: C-42.35%; | H-5.92%; | N-32.93% |
| | | found: C-41.89%; | H-5.76%; | N-31.88% |
| —NH(CH₂)₃OH | 37% | calc.: C-45.64%; | H-6.57%; | N-30.42% |
| | | found: C-45.70%; | H-6.65%; | N-29.32% |
| —NHCH₂CHOH<br>    \|<br>    CH₃ | 54% | calc.: C-45.64%; | H-6.57%; | N-30.42% |
| | | found: C-45.07%; | H-6.70%; | N-30.40% |
| —NHCH₂C(CH₃)₂OH | 58% | calc.: C-48.47%; | H-7.12%; | N-28.27% |
| | | found: C-48.45%; | H-7.14%; | N-28.20 |
| —NH—⟨H⟩—OH | 54% | calc.: C-53.86%; | H-7.19%; | N-24.98 |
| | | found: C-53.58%; | H-7.66%; | N-24.95% |
| —NHCH₂CH₂N(C₂H₅)₂ | 38% | calc.: C-53.31%; | H-8.50%; | N-31.09% |
| | | found: C-53.78%; | H-8.72%; | N-30.60% |
| —NHCH₂COOC₂H₅ | 46% | calc.: C-45.28%; | C-5.70%; | N-26.40% |
| | | found: C-45.37%; | C-5.96%; | N-25.35% |
| NHCH₂CH₂COOC₂H₅ | 44.5% | calc.: C-47.78%; | C-6.24%; | N-24.77% |
| | | found: C-46.90%; | C-6.17%; | N-23.80% |
| —NHCH₂CH₂SCH₃ | 31% | calc.: C-42.00%; | C-6.00%; | N-28.01% |
| | | found: C-41.53%; | C-6.24%; | N-27.07% |
| —NHCH₂CH₂SC₂H₅ | 43% oily substance | calc.: C-44.84%; | C-6.59%; | N-26.15% |
| | | found: C-44.75%; | C-6.71%; | N-25.75% |
| —NHCH₂CHCN<br>    \|<br>    CH₃ | 56% | calc.: C-49.74%; | C-6.00%; | N-36.27% |
| | | found: C-49.22%; | C-6.17%; | N-35.64% |
| —NHCH₂CH₂COOH | 54.5% | calc.: C-48.98%; | C-6.12%; | N-28.57% |
| | | found: C-49.64%; | C-6.21%; | N-27.89% |
| —NHCH₂CH₂NHC₆H₅ | 61.5% | calc.: C-58.78%; | C-6.12%; | N-28.57% |
| | | found: C-58.21%; | C-6.27%; | N-27.44% |
| —NHCH₂CH₂NHCOCH₃ | 51% | calc.: C-45.49%; | C-6.20%; | N-33.16 % |
| | | found: C-45.22%; | C-6.29%; | N-32.20% |
| —NH(CH₂)₃CONH)₂ | 31% | calc.: C-45.50%; | C-6.16%; | N-33.18% |
| | | found: C-46.01%; | C-6.42%; | N-31.94% |
| —NH(CH₂)₃SO₂NH₂ | 42.5% | calc.: C-34.01%; | C-4.86%; | N-28.34% |
| | | found: C-34.44%; | C-5.04%; | N-27.80% |

EXAMPLE B

5-Amino-2-(2'-ethylsulfinyl-ethylamino)-4-hydroxy-pyrimidine 3.2 gm of 5-amino-2-(2'-ethylmercapto-ethylamino)4-hydroxy-pyrimidine (0.015 mol) were dissolved in a mixture of 60 ml of absolute methanol and 60 ml of absolute methylene chloride. The solution was admixed with a solution of 2.89 gm (0.015 mol) of m-chloro-perbenzoic acid in 50 ml of methylene chloride at −15° C. After stirring for 8 hours at 0° C., the mixture was evaporated in vacuo to nearly dryness and was fractionated on a silicagel column with a methylene chloride/methanol mixture of at first 10:1, then 5:1. 1.42 gm (41.1%) of a uniform product were obtained.

Analysis: Calc.: C-41.71%; H-6.13%; N-24.33%; Found: C-41.44%; H-6.12%; N-24.48%.

IR spectrum: 1650, 1610, 1530, 1010 cm⁻¹;

NMR spectrum (DMSO+CD₃OD) signals at ppm: 1.5 (t,3H), 2.8 (m,4H), 3.4 (t,2H), 7.1 (s,1H).

Analagously, 5-amino-2-(3'-methylsulfinyl-propylamino)-4-hydroxy-pyrimidine was prepared. Yield: 36.5%

Analysis: Calc.: C-41.72%; H-6.13%; N-24.33%; Found: C-41.99%; H-6.24%; N-23.60%.

NMR spectrum (DMSO+CD₃OD) signals at ppm: 1.8 (m,2H), 2.4 (s,3H), 2.8 (t,2H), 3.4 (t,2H), 7.05 (s,1H).

EXAMPLE C

D-α-[3-(4-hydroxy-2-{2'-methoxyethylamino}-5-pyrimidinyl)-ureido]-phenylglycine 1.84 gm (0.01 mol) of 5-amino-4-hydroxy-2-(2'-methoxyethylamino)-pyrimidine were dissolved in absolute tetrahydrofuran, the solution was mixed with 1.35 ml of triethylamine, and the mixture was added dropwise to a solution of 1.05 gm of phosgene in 30 ml of tetrahydrofuran while cooling with ice. Subsequently the mixture was evaporated in vacuo to about 50 ml and added dropwise, while cooling with ice to a solution of 1.51 gm (0.01 mol) of D-phenylglycine, which was water-solubilized with 10 ml of 1 N sodium hydroxide in a 1:1 mixture of tetrahydrofuran. After stirring for 2 hours at room temperature, the pH value was kept at about 9 by the addition of 0.1 N sodium hydroxide.

Subsequently, the tetrahydrofuran was removed in vacuo. The aqueous solution was extracted twice with 100 ml each of ethyl acetate at pH 7, acidified to pH 3.1, and the precipitated product was suction-filtered off. After drying over phosphorus pentoxide, 2.06 gm (57%) of a colorless solid product were obtained.

IR spectrum: 1720 (shoulder), 1680 (broad), 1550, 1570 cm$^{-1}$;

NMR spectrum (DMSO+CD$_3$OD) signals at ppm: 3.3 (2H), 3.5 (3H), 3.6 (2H), 5.2 (1H), 7.3 (5H), 8.15 (1H).

Analysis: Calc.: C-53.18%; H-9.90%; N-19.39%; Found: C-54.02%; H-10.11%; N-18.78%;

D-α-[3-(2-(2'-ethylmercapto-ethylamino)-4-hydroxy-5-pyrimidinyl)-ureido]-p-phenylglycine was synthesized in analogous manner.

EXAMPLE D

D,L-α-[3-(4-hydroxy-2-(3'-hydroxypropylamino)-5-pyrimidinyl)-ureido]-thienylglycine (a) A mixture of 1.84 gm (0.01 mol) of 5-amino-4-hydroxy-2-(3'-hydroxypropylamino)-pyrimidine and 7 ml of diethylaminotrimethylsilane was heated for 10 minutes at 80° C. The formed solution was evaporated to dryness in vacuo, and the residual solid product was dissolved in 30 ml of absolute tetrahydrofuran. This solution was added dropwise at 0° C. to a solution of 1.05 gm of phosgene in 50 ml of dry tetrahydrofuran. After stirring for 15 minutes at room temperature, the reaction mixture was evaporated in vacuo to about 40 ml.

(b) 1.57 gm of D,L-thienylglycine were dissolved in a mixture of 50 ml of tetrahydrofuran and 10 ml of 1 N sodium hydroxide and the solution obtained in (a) was added dropwise thereto while cooling with ice. The pH value was kept to 8.0 by addition of 1 N sodium hydroxide. After the dropwise addition, the reaction mixture was stirred for 1 hour at 5° C. and 1 hour at room temperature.

Further processing was effected analogous to Example C.

Yield: 2.55 gm (69.5%); IR spectrum: 1720, 1675, 1545, 1470 cm$^{-1}$; NMR spectrum (DMSO+CD$_3$OD) signals at ppm: 1.8 (m,2H), 3.45 (m,4H), 5.5 (s,1H), 6.9 (broad, 2H), 7.25 (d,1H), 8.05 (s,1H).

Analysis: Calc.: C-45.78%; H-4.63%; N-19.07%; S-8.72%; Found: C-46.12%; H-4.90%; N-18.77%; S-8.22%.

II. PREPARATION OF END PRODUCTS

EXAMPLE 1

D-α-[3-(4-hydroxy-2-{2'-methoxyethylamino}-5-pyrimidinyl)-ureido]-p-hydroxybenzyl-penicillin sodium (a) 920 mgm of 5-amino-2-(2'-methoxyethylamino)-4-hydroxy-pyrimidine (0.005 mol) were dissolved, while heating, in 250 ml of absolute tetrahydrofuran, and the solution was mixed with 500 mgm of triethylamine. This solution was added dropwise to a solution of 500 mgm of phosgene in 30 ml of absolute tetrahydrofuran at 0° C. After stirring for 30 minutes while cooling with ice, the excess phosgene was removed by blowing nitrogen through the suspension.

(b) 2.1 gm of amoxicillin trihydrate (0.005 mol) were suspended in 80 ml of aqueous 80% tetrahydrofuran, the suspension was cooled to 0° C. and a sufficient amount of triethylamine was added to form a solution. Within 5 minutes the suspension obtained in (a) was added dropwise, while the pH value was kept to 7.5 by addition of triethylamine. 30 ml of water were added, and the reaction mixture was kept for 1 hour at 0°-2° C. Cooling was removed, and the mixture was stirred for one hour at room temperature.

Subsequently, 40 ml of water were added, and the tetrahydrofuran was removed in vacuo. The residual aqueous phase was washed twice with 50 ml of ethyl acetate. Then, 2 N hydrochloric acid was added to the solution while slowly stirring until a pH value of 2.9 was obtained, while keeping the temperature below 5° C. The precipitated product was suction-filtered off and dried in an exsiccator. A solution of 700 mgm of sodium hexanoate in 25 ml of methanol was added to the solid product, and the obtained solution was mixed with ether. The precipitated sodium salt was suction-filtered off and dried in vacuo.

Yield: 2.14 gm (71.2%).

IR spectrum: 1765, 1660, 1610, 1540 cm$^{-1}$;

NMR spectrum (DMSO+CD$_3$OD) signals at ppm: 1.5 (d,6H), 3.3 (s,3H), 3.5 (m,4H), 4.0 (s,1H), 5.4 (q,2H), 5.5 (s,1H), 6.8 (d,2H), 7.3 (d,2H), 8.15 (s,1H).

EXAMPLE 2

D-α-[3-(2-{2'-ethoxyethylamino}-4-hydroxy-5-pyrimidinyl)-ureido]-p-hydroxy-benzylpenicillin sodium This penicillin was prepared analogous to Example 1, starting from 1.68 gm (0.004 mol) of amoxicilline trihydrate and the reaction product of 790 mgm (0.004 mol) of 5-amino-2-(2'-ethoxyethylamino)-4-hydroxy pyrimidine with 400 mgm of phosgene and 0.53 ml of triethylamine.

Yield: 1.58 gm of sodium salt (64.2%);

IR spectrum: 1770, 1660, 1610, 1550, 1510 cm$^{-1}$;

NMR spectrum (DMSO+CD$_3$OD) signals at ppm: 1.15 (t,3H), 1.55 (d,6H), 3.6 (m,6H), 4.06 (s,1H), 5.45 (m,3H), 6.8 (d,2H), 7.3 (d,2H), 8.15 (s,1H).

EXAMPLE 3

D-α-[3-(2-{2'-ethoxyethylamino}-4-hydroxy-5-pyrimidinyl)-ureido]-benzylpenicillin sodium This penicillin was prepared analogous to Example 1, starting from 2.25 gm (0.006 mol) of ampicillin sodium and the reaction product of 1.19 gm (0.006 mol) of the pyrimidine of the Example 2 with 600 mgm of phosgene and 0.8 ml of triethylamine.

Yield: 2.11 gm of sodium salt (59%); IR spectrum: 1765, 1650, 1610, 1545 cm$^{-1}$; NMR spectrum (DMSO+CD$_3$OD) signals at ppm: 1.15 (t,3H), 1.50 (d,6H), 3.65 (m,6H), 4.05 (s,1H), 5.45 (q,2H), 5.55 (s,1H), 7.4 (m,5H), 8.10 (s,1H).

EXAMPLE 4

D-α-[3-(4-hydroxy-2-{2'-propoxyethylamino}-5-pyrimidinyl)-ureido]-p-hydroxy-benzylpenicillin sodium This penicillin was prepared analogous to Example 1, starting from 2.1 gm of amoxicillin trihydrate (0.005 mol) and the reaction product of 1.13 gm of 5-amino-4-hydroxy-2-(2'-propoxyethylamino)-pyrimidine with 500 mgm of phosgene and 0.68 ml of triethylamine.

Yield: 1.8 gm of sodium salt (57.5%);

IR spectrum: 1765, 1650, 1615, 1545 cm$^{-1}$;

NMR spectrum (DMSO+CD$_3$OD) signals at ppm: 1.0 (t,3H), 1.45 (m,2H), 1.55 (d,6H), 3.55 (m,6H), 4.05 (s,1H), 5.45 (q,2H), 5.5 (s,1H), 6.8 (d,2H), 7.3 (d,2H), 8.15 (s,1H).

EXAMPLE 5

D-α-[3-(2-{2'-butoxyethylamino}-4-hydroxy-5-pyrimidinyl)-ureido]-p-hydroxy-benzylpenicillin sodium This penicillin was prepared analogous to Example 1, starting from 840 mgm of amoxicillin trihydrate (0.002 mol) and the reaction product of 450 mgm (0.002 mol) of 5-amino-2-(2'-butoxyethylamino)-4-hydroxy-pyrimidine with 200 mgm of phosgene and 0.27 ml of triethylamine.

Yield: 615 mgm of sodium salt (48%); IR spectrum: 1770, 1650, 1615, 1550 cm$^{-1}$; NMR spectrum (DMSO+CD$_3$OD) signals at ppm: 0.9 (t,3H), 1.4 (m,4H), 1.6 (d,6H), 3.5 (m,6H), 4.05 (s,1H), 5.45 (m,3H), 6.8 (d,2H), 7.35 (d,2H), 8.2 (s,1H).

EXAMPLE 6

D-α-[3-(4-hydroxy-2-{3'-methoxypropylamino}-5-pyrimidinyl)-ureido]-p-hydroxy-benzylpenicillin sodium This penicillin was prepared analogous to Example 1, starting from 2.1 gm of amoxixillin trihydrate (0.005 mol) and the reaction product of 1.0 gm (0.005 mol) of 5-amino-4-hydroxy-2-(3'-methoxypropylamino)-pyrimidine with 0.5 gm of phosgene and 0.68 ml of triethylamine.

Yield: 1.82 gm of sodium salt (60%);

IR spectrum: 1765, 1650, 1600, 1500 cm$^{-1}$;

NMR spectrum (DMSO+CD$_3$OD) signals at ppm: 1.55 (d,6H), 1.8 (m,2H), 3.2–3.6 (m,7H), 4.05 (s,1H), 5.4 (q,2H), 5.5 (s,1H), 6.8 (d,2H), 7.35 (d,2H), 8.15 (s,1H).

EXAMPLE 7

D-α-[3-(4-hydroxy-2-{3'-methoxypropylamino}-5-pyrimidinyl)-ureido]-benzylpenicillin sodium This penicillin was prepared analogous to Example 1, starting from 4.5 gm (0.012 mol) of ampicillin sodium and the reaction product of 2.4 gm (0.012 mol) of the pyrimidine of Example 6 with 1.25 gm of phosgene and 1.65 ml of triethylamine.

Yield: 4.6 gm of sodium salt (66%);

IR spectrum: 1765, 1650, 1610, 1510 cm$^{-1}$;

NMR spectrum (DMSO+CD$_3$OD) signals at ppm: 1.55 (d,6H), 1.85 (m,2H), 3.2–3.65 (m,7H), 4.0 (s,1H), 5.45 (q,2H), 5.6 (s,1H), 7.35 (m,5H), 8.10 (s,1H).

EXAMPLE 8

D-α-[3-(2-{3'-ethoxypropylamino}-4-hydroxy-5-pyrimidinyl)-ureido]-p-hydroxy-benzylpenicillin sodium This penicillin was prepared analogous to Example 1, starting from 1.89 gm (0.0045 mol) of amoxicillin trihydrate and the reaction product of 950 mgm (0.0045 mol) of 5-amino-2-(3'-ethoxypropylamino)-4-hydroxypyimidine with 450 mgm of phosgene and 450 mgm of triethylamine.

Yield: 1.9 gm of sodium salt (68%);

IR spectrum: 1770, 1670, 1610, 1550, 1510 cm$^{-1}$;

NMR spectrum (DMSO+CD$_3$OD) signals at ppm: 1.05 (t,3H), 1.55 (d,6H), 1.7 (m,2H), 3.4 (m,6H), 4.05 (s,1H), 5.45 (q+s, 3H), 6.8 (d,2H), 7.35 (d,2H), 8.10 (s,1H).

EXAMPLE 9

D-α-[3-(4-hydroxy-2-{3'-isopropoxypropylamino}-5-pyrimidinyl)-ureido]-p-hydroxy benzylpenicillin sodium This penicillin was prepared analogous to Example 1, starting from 4.2 gm (0.01 mol) of amoxicillin trihydrate and the reaction product of 2.25 gm (0.01 mol) of 5-amino4-hydroxy-2-(3'-isopropoxypropylamino)-pyrimidine with 1.0 gm of phosgene and 1.35 ml of triethylamine.

Yield: 4.67 gm of sodium salt (73%);

IR spectrum: 1770, 1665, 1615, 1550 cm$^{-1}$;

NMR spectrum (DMSO+CD$_3$OD) signals at ppm: 1.15 (d,6H), 1.55 (d,6H), 1.80 (m,2H), 3.2–3.8 (m,5H), 4.05 (s,1H), 5.5 (q+s,3H), 6.8 (d,2H), 7.3 (d,2H), 8.15 (s,1H).

EXAMPLE 10

D-α-[3-(4-hydroxy-2-{2'-hydroxy-2'-methylpropylamino}-5-pyrimidinyl)-ureido]-p-hydroxy-benzylpenicillin sodium This penicillin was prepared analogous to Example 1, starting from 1.26 gm (0.003 mol) of amoxicillin trihydrate and the reaction product of 590 mgm of 5-amino-4-hydroxy-2-(2'-hydroxy-2'-methyl-propylamino)-pyrimidine (0.003 mol) with 300 mgm of phosgene and 0.41 ml of triethylamine.

Yield: 720 mgm of sodium salt (39.5%);

IR spectrum: 1765, 1660, 1610, 1550 cm$^{-1}$;

NMR spectrum (DMSO+CD$_3$OD) signals at ppm: 1.2 (6H), 1.55 (d,6H), 3.5 (2H), 4.05 (1H), 5.5 (q+s,3H), 6.85 (d,2H), 7.35 (d,2H), 8.15 (s,1H).

EXAMPLE 11

D-α-[3-(4-hydroxy-2-{2'-hydroxyethylamino}-5-pyrimidinyl)-ureido]-p-hydroxy-benzylpenicillin sodium 510 mgm (0.003 mol) of 5-amino-4-hydroxy-2-(2'-hydroxyethylamino)-pyrimidine were stirred with 3 ml of trimethylsilyldiethylamine at 80° C. for 15 minutes. The solution thus obtained was evaporated first in water aspirator vacuum and subsequently in high vacuum to dryness. After taking up the residue in 50 ml of absolute tetrahydrofuran, the solution was added dropwise while cooling with ice, to a solution of 300 mgm of phosgene in 20 ml of absolute tetrahydrofuran.

The further reaction with 1.26 gm of amoxicillin (0.003 mol) was effected as indicated in the previous examples.

Yield: 495 mgm of sodium salt (29%);

IR spectrum: 1770, 1665, 1615, 1550 cm$^{-1}$;

NMR spectrum (DMSO+CD$_3$OD) signals at ppm: 1.55 (d,6H), 3.5 (m,4H), 4.05 (s,1H), 5.45 (q,2H), 5.50 (s,1H), 6.85 (d,2H), 7.35 (d,2H), 8.10 (s,1H).

EXAMPLE 12

D-α-[3-(4-hydroxy-2-{2'-hydroxyethylamino}-5-pyrimidinyl)-ureido]-benzylpenicillin sodium This penicillin was synthesized analogous to Example 11, starting from 1.8 gm of ampicillin sodium (0.005 mol) and the reaction product of 500 mgm of the amine of Example 11 with 500 mgm of phosgene.

Yield: 950 mgm of sodium salt (34%);

IR spectrum: 1770, 1660, 1620, 1510 cm$^{-1}$;

NMR spectrum (DMSO+CD$_3$OD) signals at ppm: 1.50 (d,6H), 3.2–3.7 (m,4H), 4.0 (s,1H), 5.45 (q,2H), 5.60 (s,1H), 7.4 (m,5H), 8.10 (s,1H).

EXAMPLE 13

D-α-[3-(4-hydroxy-2-{3'-hydroxypropylamino-}-5-pyrimidinyl)-ureido]-p-hydroxy-benzylpenicillin sodium This penicillin was prepared analogous to Example 11, starting from 1.4 gm of amoxicillin trihydrate (0.0035 mol) and the reaction product of 650 mgm (0.0035 mol) of 5-amino-4-hydroxy-2-(3'-hydroxypropylamino)-pyrimidine with 350 mgm of phosgene.

Yield: 1.08 gm of sodium salt (59.5%);

IR spectrum: 1770, 1655, 1610, 1540 cm$^{-1}$;

NMR spectrum (DMSO+CD$_3$OD) signals at ppm: 1.55 (d,6H), 1.8 (m,2H), 3.2–3.8 (m,4H), 4.0 (s,1H), 5.4 (q+s,3H), 6.8 (d,2H), 7.3 (d,2H), 8.05 (s,1H).

EXAMPLE 14

D-α-[3-(4-hydroxy-2-{2'-hydroxypropylamino}-5-pyrimidinyl)-ureido]-p-hydroxy-benzylpenicellin sodium This penicillin was prepared analogous to Example 11, starting from 1.68 gm (0.004 mol) of amoxicillin trihydrate and the reaction product of 740 mgm (0.004 mol) of 5-amino-4-hydroxy-2-(2'-hydroxypropylamino)pyrimidine with 400 mgm of phosgene (after silylation).

Yield: 920 mgm of sodium salt (38.5%);

IR spectrum: 1770, 1660, 1610, 1550 cm$^{-1}$;

NMR spectrum (DMSO+CD$_3$OD) signals at ppm: 1.15 (d,3H), 1.55 (6H), 3.6 (m,2H), 3.9 (m,1H), 4.05 (s,1H), 5.4 (q,2H), 5.5 (s,1H), 6.8 (d,2H), 7.3 (d,2H), 8.15 (s,1H).

EXAMPLE 15

D-α-[3-(4-hydroxy-2-{2'-hydroxypropylamino}-5-pyrimidinyl)-ureido]-benzylpenicillin sodium This penicillin was prepared analogous to Example 11, starting from 800 mgm of ampicillin sodium (0.002 mol) and the reaction product of 370 mgm of the pyrimidine of Example 5 (0.002 mol) with 200 mgm of phosgene.

Yield: 520 mgm of sodium salt (45%);

IR spectrum: 1765, 1650, 1610, 1550 cm$^{-1}$;

NMR spectrum (DMSO+CD$_3$OD) signals at ppm: 1.2 (d,3H), 1.55 (d,6H), 3.55 (m,2H), 3.95 (m,1H), 4.05 (s,1H), 5.4 (q,2H), 5.55 (s,1H), 7.4 (5H), 8.15 (s,1H).

EXAMPLE 16

D-α-[3-(2-{ethoxycarbonylmethylamino}-4-hydroxy-5-pyrimidinyl)-ureido]-p-hydroxy-benzylpenicillin sodium This penicillin was prepared analogous to Example 1, starting from 1.05 gm (0.0025 mol) of amoxicillin trihydrate and the reaction product of 530 mgm of 5-amino-2-ethoxycarbonyl-methylamino-4-hydroxy-pyrimidine (0.0025 mol) with 250 mgm of phosgene and 0.34 ml of triethylamine.

Yield: 1.38 gm of sodium salt (88%);

IR spectrum: 1770, 1750, 1670, 1620, 1545, 1540 cm$^{-1}$;

NMR spectrum (DMSO+CD$_3$OD) signals at ppm: 1.2 (t,3H), 1.55 (d,6H), 3.5 (q,2H), 4.05 (s,1H), 4.15 (2H), 5.4 (q,2H), 5.45 (s,1H), 6.8 (2H), 7.3 (2H), 8.15 (1H).

EXAMPLE 17

D-α-[3-(2-{2'-ethoxycarbonylethylamino}-4-hydroxy-5-pyrimidinyl)-ureido]-p-hydroxy-benzylpencillin sodium This penicillin was prepared analogous to Example 1, starting from 840 mgm of amoxicillin trihydrate (0.002 mol) and the reaction product of 500 mgm (0.002 mol) of 5-amino-2-(2'-ethoxycarbonylethylamino)-4-hydroxypyrimidine with 200 mgm of phosgene and 0.27 ml of triethylamine.

Yield: 1.02 gm of sodium salt (80%);

IR spectrum: 1770, 1750, 1660, 1620, 1545, 1515 cm$^{-1}$;

NMR spectrum (DMSO+CD$_3$OD) signals at ppm: 1.25 (t,3H), 1.55 (d,6H), 3.4 (m,4H), 4.05 (1H), 4.15 (2H), 5.45 (q,2H), 5.50 (s,1H), 6.8 (d,2H), 7.3 (d,2H), 8.15 (s,1H).

EXAMPLE 18

D-α-[3-(2-{2'-diethylaminoethylamino}-4-hydroxy-5-pyrimidinyl)ureido]-p-hydroxy-benzylpenicillin sodium This penicillin was prepared analogous to Example 1, starting from 2.1 gm (0.005 mol) of amoxixillin trihydrate and the reaction product of 1.16 gm (0.005 mol) of 5-amino-2-(2'-diethylaminoethylamino)-4-hydroxy pyrimidine with 500 mgm of phosgene and 0.68 ml of triethylamine. The further processing was changed in the following way: The aqueous phase was extracted twice with 50 ml each of n-butanol at a pH of 3.4. The butanol was removed in a high vacuum, and the residue was converted into the sodium salt in conventional manner.

Yield: 1.22 gm of sodium salt (38%);

IR spectrum: 1770, 1660, 1610, 1550 cm$^{-1}$;

NMR spectrum (DMSO+CD$_3$OD) signals at ppm: 1.2–1.7 (m,12H), 3.1–3.7 (m,8H), 4.05 (s,1H), 5.5 (m,3H), 6.85 (d,2H), 7.35 (d,2H), 8.20 (s,1H).

EXAMPLE 19

D-α-[3-(4-hydroxy-2-{2'-phenoxyethylamino}-5-pyrimidinyl)-ureido]-p-hydroxy-benzylpenicillin sodium This penicillin was prepared analogous to Example 1, starting from 1.6 gm of amoxicillin trihydrate (0.004 mol) and the reaction product of 985 mgm of 5-amino-4-hydroxy-1-(2'-phenoxyethylamino)-pyrimidine with 500 mgm of phosgene and 0.67 ml of triethylamine.

Yield: 2.46 gm of sodium salt (72.5%);

IR spectrum: 1770, 1660, 1610, 1550 cm$^{-1}$;

NMR spectrum (DMSO+CD$_3$OD) signals at ppm: 1.55 (d,6H), 3.7 (m,2H), 4.05 (s,1H), 4.1 (m,2H), 5.45 (m,3H), 6.8–7.4 (m,9H), 8.15 (s,1H).

EXAMPLE 20

D-α-[3-(2-{2'-acetylaminoethylamino}-4-hydroxy-5-pyrimidinyl)-ureido]-p-hydroxy-benzylpenicillin sodium This penicillin was prepared anologous to Example 11, starting from 1.26 gm (0.003 mol) of amoxicillin trihydrate and the reaction product of 630 mgm (0.003 mol) of 2-(2'-acetylaminoethylamino)-5-amino-4-hydroxy-pyrimidine with 300 mgm of phosgene.

Yield: 865 mgm of sodium salt (46.5%);

IR spectrum: 1770, 1660, 1610, 1550 cm$^{-1}$;

NMR spectrum (DMSO+CD$_3$OD) signals at ppm: 1.55 (d,6H), 1.95 (s,3H), 2.7 (m,2H), 3.5 (m,2H), 4.05 (s,1H), 5.45 (m,3H), 6.8 (d,2H), 7.3 (d,2H), 8.05 (s,1H).

EXAMPLE 21

D-α-[3-(2-{2'-ethylsulfinylethylamino}-4-hydroxy-5-pyrimidinyl)-ureido]-p-hydroxy-benzylpenicillin sodium This penicillin was prepared analogous to Example 11, starting from 420 mgm (0.001 mol) of amoxicillin trihydrate and 230 mgm of 5-amino-2-(2'-ethylsulfinylethylamino)-4-hydroxy-pyrimidine, which was reacted with 100 mg of phosgene after silylation.

Yield: 265 mgm of sodium salt (41%);
IR spectrum: 1765, 1660, 1610, 1545 cm$^{-1}$;
NMR spectrum (DMSO+CD$_3$OD) signals at ppm: 1.3 (t,3H), 1.55 (d,6H), 3.1 (m,4H), 3.5 (m,2H), 4.05 (s,1H), 5.45 (q,2H), 5.50 (s,1H), 6.85 (2H), 7.35 (2H), 8.15 (1H).

EXAMPLE 22

D-α-[3-(2-{2'-acetylethylamino}-4-hydroxy-5-pyrimidinyl)-ureido]-p-hydroxy-benzylpenicillin sodium This penicillin was prepared analogous to Example 1, starting from 4.2 gm of amoxicillin trihydrate (0.01 mol) and the reaction product of 1.96 gm (0.01 mol) of 2-(2'-acetylethylamino)-5-amino-4-hydroxy-pyrimidine with 1.01 gm of phosgene and 1.35 ml of triethylamine.

Yield: 3.17 gm of sodium salt (52%);
IR spectrum: 1770, 1680, 1660, 1610, 1545 cm$^{-1}$;
NMR spectrum (DMSO+CD$_3$OD) signals at ppm: 1.55 (d,6H), 2.2 (s,3H), 2.7 (m,2H), 3.4 (m,2H), 4.05 (1H), 5.45 (q,2H), 5.50 (s,1H), 6.85 (2H), 7.35 (2H), 8.15 (1H).

EXAMPLE 23

D-α-[3-(4-hydroxy-2-{2'-methylmercaptoethylamino}-5-pyrimidinyl)-ureido]-p-hydroxy-benzylpenicillin sodium This penicillin was prepared analogous to Example 1, starting from 2.1 gm of amoxicillin trihydrate (0.005 mol) and the reaction product of 1.03 gm of 5-amino-4-hydroxy-2-(2'-methylmercaptoethylamino)-pyrimidine 0(0.005 mol) with 500 mgm of phosgene and 0.67 ml of triethylamine.

Yield: 2.35 gm of sodium salt (75%);
IR spectrum: 1770, 1660, 1610, 1550 cm$^{-1}$;
NMR spectrum (DMSO+CD$_3$OD) signals at ppm: 1.55 (d,6H), 2.3 (s,3H), 2.7 (m,2H), 3.4 (m,2H), 4.05 (s,1H), 5.45 (q,2H), 5.5 (s,1H), 6.85 (d,2H), 7.35 (d,2H), 8.15 (s,1H).

EXAMPLE 24

D-α-[3-(2-{2'-ethylmercaptoethylamino}-4-hydroxy-5-pyrimidinyl)-ureido]-p-hydroxy-benzylpenicillin sodium This penicillin was prepared analogous to Example 1, starting from 1.26 gm (0.003 mol) of amoxixillin trihydrate and the reaction product of 640 mgm of 5-amino-2-(2'-ethylmercaptoethylamino)-4-hydroxy-pyrimidine (0.003 mol) with 300 mgm of phosgene and 0.41 ml of triethylamine. During further processing the corresponding penicillin was extracted with ethyl acetate at pH 2.7. After drying over sodium sulfate, the ethyl acetate was removed in vacuo. The residual end product was converted into the sodium salt in conventional manner.

Yield: 1.31 gm of sodium salt (69.5%);
IR spectrum: 1770, 1660, 1610, 1540, 1515 cm$^{-1}$;
NMR spectrum (DMSO+CD$_3$OD) signals at ppm: 1.25 (t,3H), 1.55 (6H), 2.65 (m,4H), 3.5 (m,2H), 4.05 (s,1H), 5.4 (q,2H), 5.5 (s,1H), 6.8 (2H), 7.3 (2H), 8.15 (1H).

EXAMPLE 25

D-α-[3-(2-{2'-cyano-propylamino}-4-hydroxy-5-pyrimidinyl)-ureido]-p-hydroxy-benzylpenicillin sodium This penicillin was prepared analogous to Example 11, starting from 4.2 gm of amoxicillin trihydrate (0.01 mol) and 1.93 gm (0.01 mol) of 5-amino-2-(2'-cyano-propylamino)-4-hydroxy pyrimidine, which was reacted with 1.01 gm of phosgene after silylation.

Yield: 3.6 gm of sodium salt (59%);
IR spectrum: 1765, 1650, 1600, 1545 cm$^{-1}$;
NMR spectrum (DMS0+CD$_3$OD) signals at ppm: 1.2 (d,3H), 1.55 (d,6H), 2.8 (m,1H), 3.5 (m,2H), 5.4 (q,2H), 5.5 (s,1H), 6.8 (d,2H), 7.3 (d,2H), 8.10 (s,1H).

EXAMPLE 26

D-α-[3-(4-hydroxy-2-{4'-hydroxy-cyclohexylamino}-5-pyrimidinyl)-ureido]-p-hydroxy-benzylpenicillin sodium This penicillin was prepared analogous to Example 11, starting from 1.68 gm (0.004 mol) of amoxicillin trihydrate and the reaction product of 500 mgm (0.004 mol) of 5-amino-4-hydroxy-2-(4'-hydroxy-cyclohexylamino)-pyrimidine with 400 mgm of phosgene.

Yield: 1.63 gm of sodium salt (64%);
IR spectrum: 1770, 1660, 1615, 1550 cm$^1$;
NMR spectrum (DMSO+CD$_3$OD) signals at ppm: 1.2–2.2 (m,1H), 3.65 (m,1H), 3.95 (m,1H), 4.05 (s,1H), 5.45 (q,2H), 5.50 (s,1H), 6.8 (d,2H), 7.3 (d,2H), 8.15 (s,1H).

EXAMPLE 27

D-α-[3-(4-hydroxy-2-{4'-hydroxy-cyclohexylamino}-5-pyrimidinyl)-ureido]-benzylpenicillin sodium This penicillin was prepared analogous to Example 11, starting from 3.75 gm (0.01 mol) of ampicillin trihydrate and the reaction product of 2.24 gm (0.01 mol) of the pyrimidine of Example 26 with 1.01 gm of phosgene.

Yield: 3.62 gm of sodium salt (58%);
IR spectrum: 1765, 1655, 1615, 1545 cm$^{-1}$;
NMR spectrum (DMSO=CD$_3$OD) signals at ppm: 1.15–2.1 (m,14H), 3.7–4.0 (m,1H+1H), 4.05 (s,1H), 5.40 (q,2H), 5.55 (s,1H), 7.4 (m,5H), 8.15 (1H).

EXAMPLE 28

D-α-[3-(2-{2'-anilino-ethylamino}-4-hydroxy-5-pyrimidinyl)-ureido]-p-hydroxy-benzylpenicillin sodium This penicillin was prepared analogous to Example 1, starting from 2.1 gm of amoxicillin trihydrate (0.005 mol) and the reaction product of 1.23 gm of 5-amino-2-(2'-anilino-ethylamino)-4-hydroxy pyrimidine (0.005 mol) with 500 mgm of phosgene and 0.68 ml of triethylamine.

Yield: 2.06 gm of sodium salt (61%);
IR spectrum: 1765, 1660, 1610, 1545 cm$^{-1}$;

NMR spectrum (DMSO+CD₃OD) signals at ppm: 1.55 (d,6H), 3.2–3.8 (m,4H), 4.05 (1H), 5.45 (q,2H), 5.50 (s,1H), 6.8–7.45 (m,9H), 8.20 (s,1H).

EXAMPLE 29

D-α-[3-(2-{3'-aminocarbonylpropylamino}-4-hydroxy-5-pyrimidinyl)-ureido]-p-hydroxy-benzylpenicillin sodium Preparation analogous to Example 11, starting from 1.1 gm (0.0026 mol) of amoxicillin trihydrate and 550 mgm (0.0025 mol) of 5-amino-2-(3'-aminocarbonylpropylamino)-4-hydroxy-pyrimidine, which was reacted with 260 mgm of phosgene in tetrahydrofuran after silylation.

Yield: 740 mgm of sodium salt (47%);

IR spectrum: 1765, 1660, 1615, 1550 cm⁻¹;

NMR spectrum (DMSO+CD₃OD) signals at ppm: 1.55 (d,6H), 1.9 (t,2H), 2.8 (m,2H), 3.45 (m,2H), 4.05 (s,1H), 5.45 (q,2H), 5.50 (s,1H), 6.8 (d,2H), 7.35 (d,2H), 8.15 (s,1H).

EXAMPLE 30

D-α-[3-(2-{3'-aminosulfonylpropylamino}-4-hydroxy-5-pyrimidinyl)-ureido]-p-hydroxy-benzylpenicillin sodium Preparation analogous to Example 11. 2.1 gm of amoxicillin trihydrate (0.005 mol) were reacted with the reaction product of 1.5 gm (0.005 mol) of 5-amino-2-(3'-aminosulfonyl-propylamino)-4-hydroxy-pyrimidine, 5 ml of trimethylsilyldiethylamine and 500 mgm of phosgene.

Yield: 1.84 gm (56.6%);

IR spectrum: 1770, 1660, 1610, 1560, 1300, 1160 cm⁻¹;

NMR spectrum (DMSO+CD₃OD) signals at ppm: 1.55 (d,6H), 2.0 (m,2H), 2.85 (m,2H), 3.40 (m,2H), 4.05 (s,1H), 5.45 (q,2H), 5.50 (s,1H), 6.85 (d,2H), 7.35 (d,2H), 8.15 (s,1H).

EXAMPLE 31

D-α-[3-(4-hydroxy-2-{2'-methoxyethylamino}-5-pyrimidinyl)-ureido]-benzylpenicillin sodium 10 mgm of N-methyl-morpholine were added to a suspension of 1.94 gm (0.005 mol) of D-α-[3-(4-hydroxy-2-{2'-methoxyethylamino}-5-pyrimidinyl)-ureido]-phenylglycine sodium salt in 25 ml of anhydrous acetone. The reaction mixture was cooled to −20° to −15° C. and at this temperature a solution of 550 mg of ethyl chloroformate (0.005 mol) in 10 ml of anhydrous acetone was added. After stirring for one hour at −20° C., a solution of 1.6 gm of the triethylammonium salt of the 6-amino-penicillanic acid in 10 ml of anhydrous methylene chloride was added dropwise at this temperature. The reaction mixture was stirred for one hour at −20° C., one hour at 0° C. and one hour at room temperature. After removing the organic solvent in vacuo, the residue was dissolved in a mixture of 40 ml of water and 60 ml of ethyl acetate at a pH of 7.0. The aqueous phase was separated and was adjusted to a pH of 2.9 by addition of dilute hydrochloric acid while cooling with ice. The precipitated solid product was suction-filtered off and dried in vacuo. The sodium salt was prepared by addition of sodium ethyl-hexanoate.

Yield: 2.05 gm (70%);

IR spectrum: 1770, 1660, 1610, 1545, 1515 cm⁻¹;

NMR spectrum (DMSO+CD₃OD) signals at ppm: 1.55 (d,6H), 3.3 (s,3H), 3.5 (m,4H), 4.1 (s,1H), 5.5 (q,2H), 5.55 (s,1H), 7.5 (m,5H), 8.1 (s,1H).

EXAMPLE 32

D-α-[3-(2-{2'-ethylmercapto-ethylamino}-4-hydroxy-5-pyrimidinyl)-ureido]-benzylpenicillin sodium 2.16 gm (0.01 mol) of anhydrous 6-aminopenicillanic acid were silylated with 2.5 ml of N,O-(bistrimethylsilyl)-acetamide at room temperature in dry dimethylformamide. At −10° C. the obtained solution was added dropwise to a solution (see also Example 31) prepared at −20° C. from 3.9 gm (0.01 mol) of D-α-[3-{2'-ethylmercaptoethylamino}-4-hydroxy-5-pyrimidinyl-ureido]-phenylglycine, 1.1 gm of ethyl chloroformate and 1.05 gm of N-methylmorpholine. Further reaction and processing see Example 31.

Yield: 2.8 gm of sodium salt (46%);

IR spectrum: 1770, 1660, 1610, 1550 cm⁻¹;

NMR spectrum (DMSO+CD₃OD) signals at ppm: 1.25 (t,3H), 1.55 (d,6H), 2.7 (m,4H), 3.45 (t,2H), 4.0 (s,1H), 5.4 (q,2H), 5.55 (s,1H), 7.4 (m,5H) 8.15 (s,1H).

EXAMPLE 33

D,L-α-[3-(2-{3'-hydroxypropylamino)-4-hydroxy-5-pyrimidinyl)-ureido]-thienylmethylpenicillin sodium Preparation analogous to Example 32, starting from 1.84 gm (0.005 mol) of the ureido-carboxylic acid of Example D and 1.08 gm (0.005 mol) of 6-amino-penicillanic acid.

Yield: 1.53 gm (52.5%);

IR spectrum: 1765, 1660, 1615, 1550 cm⁻¹;

NMR spectrum (DMSO+CD₃OD) signals at ppm: 1.55 (d,6H), 1.8 (m,2H), 3.5 (m,4H), 4.05 (s,1H), 5.5 (m,2H), 5.7 (s,1H), 6.9 (broad s,2H), 7.30 (d,1H), 8.1 (s,1H).

The compounds embraced by formulas I and I' and their non-toxic, pharmacologically acceptable salts formed with inorganic and organic bases have useful pharmacodynamic properties. More particularly, they exhibit broad-spectrum antibiotic activity, both in vivo and in vitro, against pathogenic microorganisms, especially against gram-positive and gram-negative bacteria. After parenteral or peroral administration to warm-blooded animals, such as mice, high levels of the compounds of this invention are found in tissue, serum, organs and urine. The antibacterial activity of the compounds of this invention was determined and compared to a known penicillin by the test methods described below, and Tables I and II show the results obtained for a few representative species of the invention, where A = the compound of Example 1 (A = p-hydroxyphenyl); R = —NH—CH₂—OCH₃);

B = the compound of Example 13 (A = p-hydroxyphenyl; R = —NH—(CH₂)₃—OH);

C = the compound of Example 26 (A = p-hydroxyphenyl; R = —NH——OH);

D = the compound of Example 17 (A = p-hydroxyphenyl; R = —NH—CH₂—CH₂—COOC₂H₅);

E = the compound of Example 23 (A = p-hydroxyphenyl; R = —NH—CH₂—CH₂—S—C₂H₅); and F = the known pencillin (azlocillin) of the formula ATCC 10031 and 272 and *Proteus mirabilis Hamburgensis.*

The following Table I shows the determined minimum inhibitory concentrations (MIC) for compounds A–F:

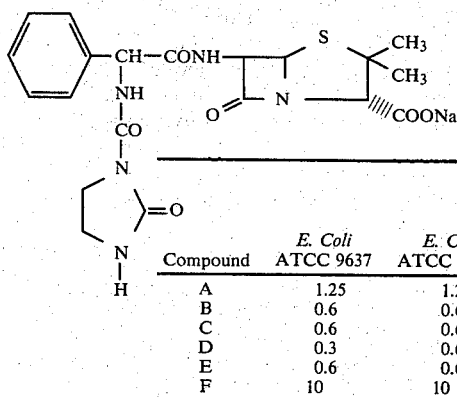

TABLE I

| | MIC values in μgm/ml. | | | | | | | | |
|---|---|---|---|---|---|---|---|---|---|
| Compound | E. Coli ATCC 9637 | E. Coli ATCC 11775 | Pseud. aerug. Walter | Pseud. aerug. hamb. | Pseud. aerug. ATCC 10145 | Serrat. marsec. | Klebs. pneum. ATCC 10031 | Klebs. pneum. 272 | Prot. mirabilis ham. |
| A | 1.25 | 1.25 | 5 | 1.25 | 1.25 | 0.6 | 20 | 40 | 0.6 |
| B | 0.6 | 0.6 | 5 | 1.25 | 1.25 | 1.25 | 10 | 10 | 0.3 |
| C | 0.6 | 0.6 | 2.5 | 2.5 | 1.25 | 1.25 | 20 | 10 | 0.08 |
| D | 0.3 | 0.6 | 2.5 | 2.5 | 2.5 | 1.25 | 10 | 10 | 0.3 |
| E | 0.6 | 0.6 | 2.5 | 2.5 | 1.25 | 0.6 | 10 | 10 | 0.08 |
| F | 10 | 10 | 10 | 10 | 5 | 5 | 40 | 40 | 1.25 |

1. In vitro tests:

The tests were performed according to the method of the serial dilution test in the microtiter system. The effect of the test substances on bacteriostasis was examined in a fluid medium. The bacteristatic activity was examined at the following concentrations: 80, 40, 20, 10, 5, 2.5, 1.25, 0.6, 0.3, 0.08 and 0.01 μgm/ml.

The nutrient medium consisted of: 10 gm of peptone, 8 gm of meat extract oxoid, 3 gm of sodium chloride, and 2 gm of sec. sodium phosphate diluted with distilled water to 1000 ml (pH 7.2–7.4). Only in the test against streptococci was 1% of glucose added. The age of the primary cultures was about 20 hours. The standardization of the microorganism suspension was effected by means of a photometer according to the method of Eppendorf (test tube diameter 14 mm, filter 546 nm), using for comparison a barium sulfate suspension formed by the addition of 3.0 ml of 1% barium chloride solution to 97 ml of 1% sulfuric acid. After the standardization, the *Streptococcus aronson* was further diluted to a concentration of 1:15 and the other microorganisms to a concentration of 1:1500 using a sodium chloride solution. 16 mgm of the test compound were placed into a 10 ml measuring flask, and the flask was filled up to the mark with the solvent. The further dilution series was standardized with distilled water or the particular solvent.

The cavities of microtiter plates were filled with 0.2 ml of nutrient medium. Then, 0.01 ml of the appropriate test compound solution was added, followed by inoculation with 0.01 ml of the standardized microorganism suspension. The bacteria were incubated at 37° C. for 18–20 hours. Control tests using only the solvent were carried out simultaneously.

The measurement was carried out macroscopically to determine the minimum inhibitory concentration (the lowest still bacteriostatically effective concentration).

As test organism were used:

*Staphylococcus aureus* SG 511, *Escherichia coli* ATCC 9637 and 11775, *Pseudomonas aeruginosa Hamburgensis*, ATCC 10145 and *Pseudomonas aeruginosa Walter*, *Serratia marcescens* ATCC 13880, *Klebsiella pneumoniae*

The above Table I shows that the compounds of this invention are significantly superior to the prior art compound in their activity against typical gram-negative bacteria found in hospitals.

Table II below shows the identity of substituents A and R in compounds of the formula I and I' which exhibited especially good antibacterial activity in vitro:

TABLE II

| A | R |
|---|---|
| phenyl | —NHCH$_2$CH$_2$OH |
| p-hydroxyphenyl | —NHCH$_2$CH$_2$OH |
| p-hydroxyphenyl | —NHCH$_2$C(CH$_3$)$_2$OH |
| p-hydroxyphenyl | —NH(CH$_2$)$_3$OH |
| phenyl | —NH(CH$_2$)$_3$OH |
| 2-thienyl | —NH(CH$_2$)$_3$OH |
| phenyl | —NHCH$_2$CH(CH$_3$)OH |
| p-hydroxyphenyl | —NHCH$_2$CH(CH$_3$)OH |
| phenyl | —NHCH$_2$CH$_2$OCH$_3$ |
| p-hydroxyphenyl | —NHCH$_2$CH$_2$OCH$_3$ |
| phenyl | —NHCH$_2$CH$_2$OC$_2$H$_5$ |
| p-hydroxyphenyl | —NHCH$_2$CH$_2$OC$_2$H$_5$ |
| phenyl | —NH(CH$_2$)$_3$OCH$_3$ |
| p-hydroxyphenyl | —NH(CH$_2$)$_3$OCH |
| p-hydroxyphenyl | —NHCH$_2$COOC$_2$H$_5$ |
| p-hydroxyphenyl | —NHCH$_2$CH$_2$COOC$_2$H$_5$ |
| phenyl | —NHCH$_2$CH$_2$SC$_2$H$_5$ |
| p-hydroxyphenyl | —NHCH$_2$CH$_2$SC$_2$H$_5$ |
| p-hydroxyphenyl | —NHCH$_2$CH$_2$SCH$_3$ |
| p-hydroxyphenyl | —NHCH$_2$CH(CH$_3$)—CN |
| p-hydroxyphenyl | —NHCH$_2$CH$_2$NHCOCH$_3$ |
| p-hydroxyphenyl | —NHCH$_2$CH$_2$CH$_2$SOCH$_3$ |
| p-hydroxyphenyl | —NHCH$_2$CH$_2$CH$_2$CONH$_2$ |
| p-hydroxyphenyl | —NHCH$_2$CH$_2$CH$_2$SO$_2$NH$_2$ |
| phenyl | —NH—⟨H⟩—OH |
| p-hydroxyphenyl | —NH—⟨H⟩—OH |
| p-hydroxyphenyl | —NHCH$_2$CH$_2$COCH$_3$ |

2. Acute toxicity:

The acute toxicity was determined by peroral and subcutaneous administration of the test compound to white mice at increasing dosage levels.

The LD$_{50}$ is the dose which leads to the death of 50% of the animals within 8 days. All test compounds showed after oral administration an LD$_{50}$ of >4 gm/kg, and after subcutaneous administration an LD$_{50}$ of >3 gm/kg, i.e. at 3 gm/kg no animals died. This means that the compounds are practically non-toxic.

3. In vivo tests:

The compounds according to the invention were tested in vivo in mice against experimental infections. As pathogenic bacteria *E.coli* ATCC 11775 and Pseudomonas aeruginosa Walter were used. An intraperitoneal infection was induced in each mouse with 0.2 ml of a 5% mucin suspension of the bacteria corresponding to about $1.4 \times 10^6$ *E. coli* germs and $1.3 \times 10^6$ pseudomonas germs/mouse. Female NMRI mice were used, divided into groups of 10 animals. Two groups were untreated and the remaining groups were treated with different doses of the penicillins to be tested to determine the $ED_{50}$ (dose at which 50% of the animals survived). The groups infected with *E. coli* were on the first day treated with the test compound three times (1.4 and 7 hours post infectionem) and on the second day twice. The groups with the pseudomonas infection were on the first day treated with the test compound 6 times (1, 3, 5, 7, 9 and 11 hours post infectionem) and on the second and third day twice.

The observation time was in both cases 7 days. The results of these tests are shown in the following Table III.

TABLE III

| In vivo activity in mice | |
| --- | --- |
| (a) *E. coli* infections (subcutaneous administration): | |
| Compound | $ED_{50}$ (mg/gk) |
| A | 2 |
| B | 0.8 |
| C | 0.7 |
| D | 4.2 |
| E | 1.7 |
| F | 35 |
| (b) Pseudomonas (subcutaneous administration): | |
| Compound | $ED_{50}$ (mg/kg) |
| A | 1.5 |
| B | 1.2 |
| C | 1.7 |
| E | 2.3 |
| F | 110 |

A significant superiority of compounds A to E is shown in comparison to the known compound F.

It was a further object of the present invention to provide pharmaceutical compositions which are useful for the treatment of infectious diseases in humans and animals.

For pharmaceutical purposes the compounds of the present invention are administered to warm-blooded animals perorally, parenterally, rectally or topically as active ingredients in customary dosage unit compositions, that is, compositions in dosage unit form consisting essentially of an inert pharmaceutical carrier and one effective dosage unit of the active ingredient.

Preferred pharmaceutical compositions include, for example, tablets, coated pills, capsules, granulates, suppositories, solutions, suspensions, emulsions, ointments, gels, creams, powders and sprays. It is of advantage to administer the active ingredient or a mixture of different active ingredients of the formula I or I' at a dosage of 5 to 500, preferably at 10 to 200 mg/kg body weight each 24 hours, optionally in form of several single doses. A single dose contains the active ingredient(s) according to the invention, preferably in amounts of about 1 to about 250, particularly 10 to 60 mg/kg body weight. Depending on the kind and the body weight of the subject to be treated, on the kind and the seriousness of the disease, on the type of composition and on the route of administration as well as on the period or interval over which the administration takes place, it may however be necessary to deviate from the above dosages. Thus, it may be sufficient in some cases to administer less than the above-mentioned amount of active ingredient, while in other cases the above-mentioned amount of active ingredient must be exceeded. The optimum dosage and route of administration of the active ingredients which are necessary in each case can easily be determined by one skilled in the art.

The compounds of this invention may also be incorporated into foodstuffs and into drinking water according to conventional methods, so as to prevent and/or cure infections by gram-negative and gram-positive bacteria and also to promote and improve utilization of the foodstuff.

The following examples illustrate a few pharmaceutical dosage unit compositions comprising a compound of the present invention as an active ingredient and represent the best modes contemplated of using the invention.

EXAMPLE 34

Tablets containing
D-α-[3-hydroxy-2-{3'-hydroxypropylamino}-5-pyrimidinyl)-ureido]-p-hydroxybenzylpenicillin sodium A mixture consisting of 2 kg of active ingredient, 5 kg. of lactose, 1.8 kg of potato starch, 0.1 kg of magnesium stearate and 0.1 kg of talcum was pressed in conventional manner into tablets, so that tablets each containing 200 mg of active ingredient were obtained.

EXAMPLE 35

Coated tablets containing
D-α-[3-(4-hydroxy-2-{3'-hydroxypropylamino}-5-pyrimidinyl)-ureido]-p-hydroxy benzylpenicillin sodium Analogous to Example I, tablets were pressed which were subsequently coated in conventional manner with a thin shell consisting of sugar, potato starch, talcum and tragacanth.

EXAMPLE 36

Capsules containing
D-α-[3-(4-hydroxy-2-{3'-hydroxypropylamino}-5-pyrimidinyl)-ureido]-p-hydroxy benzylpenicillin sodium Five kg of active ingredient were filled into hard gelatine capsules in conventional manner, so that each capsule contained 500 mg of active ingredient.

EXAMPLE 37

Dry ampules containing
D-α-[3-(4-hydroxy-2-{3'-hydroxypropylamino}-5-pyrimidinyl)-ureido]-p-hydroxy benzylpenicillin sodium 251 gm of active ingredient were dissolved under aseptic conditions in 2008 ml of distilled water suitable for injection. The solution was filtered through a Millipore filter (pore size 0.22 μm, product of Millipore Corporation, Bedford, USA). The solution was then poured in 2.0 ml portions into each of 1000 glass tubes (capacity 10 ml) and lyophilised. The glass tubes were closed with a rubber stopper and an aluminum cap. Each tube (No. A) containing 250 mg of active ingredient. 2.0 ml portions of a physiological salt solution suitable for injection were filled into ampules, and the ampules were closed. The ampules (No. B) were kept in this form. By pouring the physiological salt solution in the ampules (No. B) into glass tubes (No. A) an injectable composition for intravenous administration was obtained. 20 ml portions of distilled water suitable for injection were poured into the glass tubes (No. A), and the solution was dissolved in a 5% solution of glucose suitable for injection (250 ml). In this way a solution for continuous infusion was formed.

Any one of the other compounds embraced by formula I or I' or a non-toxic, pharmacologically acceptable salt thereof may be substituted for the particular active ingredient in Examples 34 through 37. Likewise, the amount of active ingredient in these illustrative examples may be varied to achieve the dosage unit range set forth above, and the amounts and nature of the inert pharmaceutical carrier ingredients may be varied to meet particular requirements.

We claim:
1. A compound of the formula

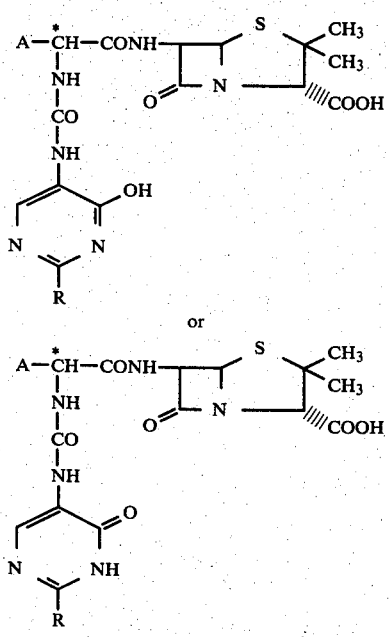

or wherein
A is phenyl, p-hydroxy-phenyl, 2-thienyl, 3-thienyl or 3,4-disubstituted phenyl, where the substituents, which may be identical to or different from each other, are each chlorine, hydroxyl or methoxy;
R is —NH—Z—X;
Z is straight or branched alkylene of 1 to 6 carbon atoms or cycloalkylene of 3 to 6 carbon atoms;

X is cyano, hydroxyl, mercapto, aminocarbonyl, aminosulfonyl,

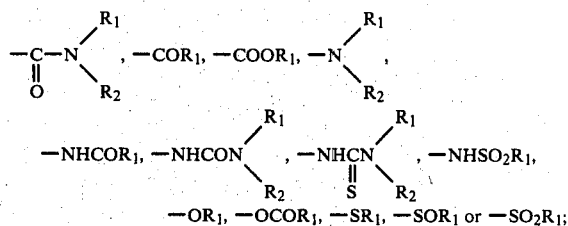

$R_1$ is straight or branched alkyl of 1 to 4 carbon atoms or phenyl; and
$R_2$ is hydrogen or alkyl of 1 to 4 carbon atoms;
or a non-toxic, pharmacologically acceptable salt thereof formed with an onorganic or organic base.

2. A compound of claim 1 which has the D=R-configuration.

3. A compound of claim 1, where
A is phenyl or p-hydroxy-phenyl;
R is 4'-hydroxy-cyclohexylamino,

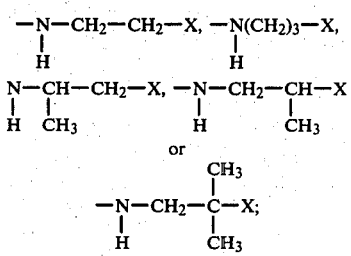

X is hydroxyl, methoxy, ethoxy, methoxycarbonyl, ethoxycarbonyl, methylcarbonyl, ethylcarbonyl, methylmercapto, ethylmercapto, aminocarbonyl, aminosulfonyl, acetylamino, methylsulfinyl or ethylsulfinyl;
or a non-toxic, pharmacologically acceptable salt thereof formed with an inorganic or organic base.

4. A compound of claim 3 which has the D=R-configuration.

5. An antibacterial pharmaceutical composition consisting essentially of an inert pharmaceutical carrier and an effective antibacterial amount of a compound of claim 1.

6. The method of destroying or suppressing the growth or reproduction of pathogenic bacteria in a warm-blooded animal, which comprises perorally, parenterally, rectally or topically administering to said animal an effective antibacterial amount of a compound of claim 1.

* * * * *

UNITED STATES PATENT AND TRADEMARK OFFICE
CERTIFICATE OF CORRECTION

PATENT NO. : 4,289,775
DATED : September 15, 1981
INVENTOR(S) : BERND WETZEL ET AL.

It is certified that error appears in the above—identified patent and that said Letters Patent is hereby corrected as shown below:

Column 1, line 63: Delete "B".

Column 9, line 20 of Table below "R": "$NHCH_2CH_2COOH$" should read -- $NHCH_2CH_2COCH_3$ --.

Column 16, line 9: "hydrox-" should read -- hydroxy- --.

Column 16, line 10: "ypyrimidine" should read -- pyrimidine --.

Column 18, line 38: "1.2-2.2 (m, 1H)" should read -- 1.2-2.2 (m, 14H) --.

Column 22, Table 1: "Serrat. marsec." should read -- Serrat. marcesc. --.

Column 24, line 24: "D-α-[3-hydroxy-2-" should read -- D-α-[3-(4-hydroxy-2- --.

Column 24, line 66: "containing" should read -- contained --.

Signed and Sealed this

Thirteenth Day of April 1982

|SEAL|

Attest:

GERALD J. MOSSINGHOFF

Attesting Officer    Commissioner of Patents and Trademarks